(12) United States Patent
Duncan et al.

(10) Patent No.: US 7,582,091 B2
(45) Date of Patent: Sep. 1, 2009

(54) OSTEOTOMY GUIDE

(75) Inventors: Clive P. Duncan, Vancouver (CA);
Laban D. Cook, Claypool, IN (US);
Robert D. Krebs, Warsaw, IN (US);
Stephen J. Vankoski, Fort Wayne, IN (US)

(73) Assignee: Zimmer Technology, Inc., Warsaw, IN (US)

( * ) Notice: Subject to any disclaimer, the term of this patent is extended or adjusted under 35 U.S.C. 154(b) by 570 days.

(21) Appl. No.: 11/230,072

(22) Filed: Sep. 19, 2005

(65) Prior Publication Data
US 2007/0083214 A1    Apr. 12, 2007

(51) Int. Cl.
*A61F 5/00* (2006.01)
(52) U.S. Cl. ...................................................... 606/87
(58) Field of Classification Search .................. 606/87, 606/89
See application file for complete search history.

(56) References Cited
U.S. PATENT DOCUMENTS
4,621,630 A * 11/1986 Kenna ........................ 606/89
4,959,066 A * 9/1990 Dunn et al. .................... 606/89
6,139,551 A * 10/2000 Michelson et al. ............ 606/79
2002/0099381 A1* 7/2002 Maroney ...................... 606/86
2004/0153062 A1 8/2004 McGinley et al.
2004/0167531 A1* 8/2004 Hodorek ...................... 606/87

OTHER PUBLICATIONS

Zimmer, Inc., *VerSys™ Hip System, Versys Cemented, Cemented Plus, and Cemented CT Hip Prostheses: Surgical Technique for Primary Hip Arthroplasty*, 97-7852-02, © 1997.
Zimmer, Inc. *Apollo® Hip System: Surgical Technique*, 1000-01-491 Feb. 2004, © 2004.

* cited by examiner

*Primary Examiner*—Eduardo C Robert
*Assistant Examiner*—Elana B Fisher
(74) *Attorney, Agent, or Firm*—Baker & Daniels LLP

(57) ABSTRACT

An osteotomy guide for indicating the femoral neck resection on a femur and its method of use are presented. The osteotomy guide includes an indexing feature for aligning the guide with an anatomic landmark and a resection guide for indicating the resection relative to the indexing feature.

7 Claims, 4 Drawing Sheets

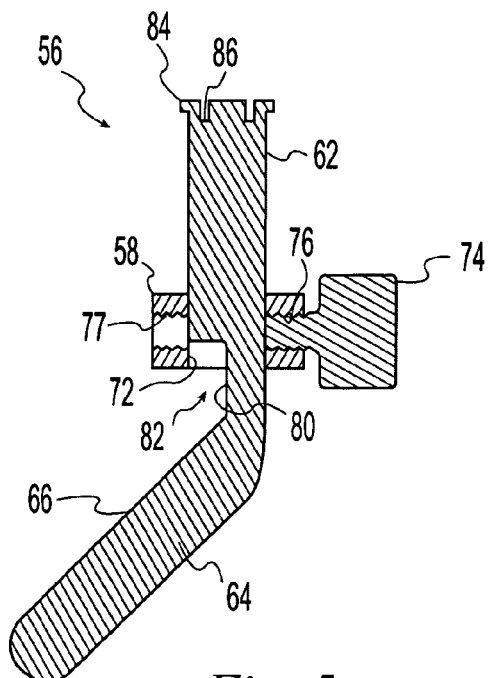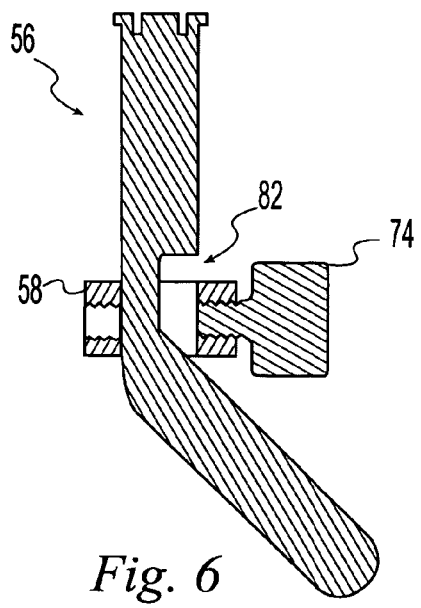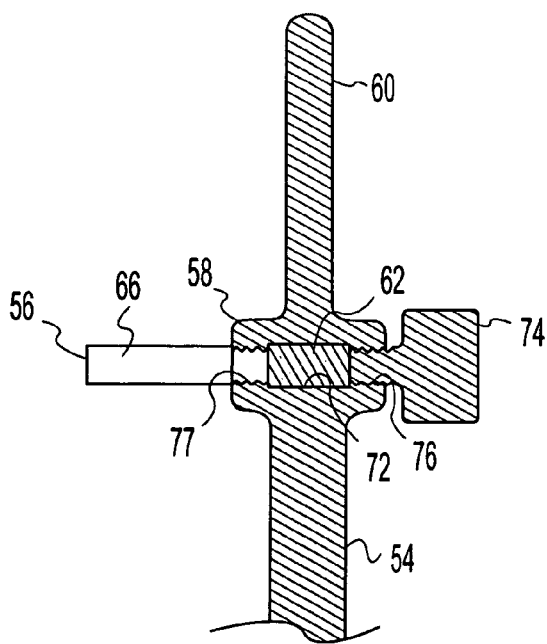

OSTEOTOMY GUIDE

FIELD OF THE INVENTION

The present invention relates to instruments for performing orthopaedic surgery. In particular, the present invention relates to instruments for gauging the resection level of the femoral head.

BACKGROUND

Total hip arthroplasty is often used to restore function to a diseased or injured hip joint. Positions and directions relative to the hip joint may be described in terms of proximal being nearer the hip joint, distal being further from the hip joint, anterior being nearer the front of the body, posterior being nearer the back of the body, medial being nearer the centerline of the body, and lateral being further from the center line of the body. In total hip arthroplasty, the surfaces of the femur and pelvis are cut away and replaced with substitute implants. In a typical case, the implants include a hip stem component, a femoral head component, an acetabular component, and bone cement.

During preoperative planning, the surgeon typically overlays images of the available implants on an X-ray of the hip joint to determine the appropriate size, offset, and head/neck length to best fit the patient's anatomy and reestablish the anatomic joint mechanics and leg length. During this preoperative planning, the surgeon determines the level for the neck resection that will properly position the implants.

The bone is prepared by first exposing the hip joint by incising and dissecting tissues down to and through the joint capsule. A flat, plate-like, osteotomy guide corresponding to the femoral implant, or at least the neck portion of the implant, is overlaid onto the bone.

The guide includes features for aligning the guide with anatomic landmarks such as the femoral head center, greater trochanter, and/or lesser trochanter. The guide further includes markings indicating the appropriate resection level to properly position the implant. Using the guide as a reference, the surgeon marks the bone at the level of the neck osteotomy with a saw or methylene blue. For example, the guide can have markings indicating the distance up from the lesser trochanter. The surgeon selects the mark that corresponds to his preoperative templating and creates a corresponding mark on the bone. The guide is removed and the neck is cut on the mark to remove the femoral head. The femur is further prepared by reaming and/or broaching the femoral canal down into the bone along an axis from a proximal position near the hip joint at the upper end of the femur toward a distal position nearer the knee joint at the lower end of the femur. The pelvis is prepared by reaming the acetabulum. The implants may be placed directly in contact with the prepared bone surfaces for bony fixation of the implant. Alternatively, bone cement may be introduced into the prepared canal and acetabulum so that it hardens around and locks the components in place.

A recent development is the use of minimally invasive surgical techniques in which the bone is prepared and the implants inserted through small incisions that cause less trauma to surrounding muscles and other soft tissues such that the patient's recovery is faster. Such minimally invasive surgical techniques can be challenging due to the difficulty in visualizing the surgical cavity and maneuvering the instruments and implants within the tight confines of the incision.

SUMMARY

The present invention provides an osteotomy guide and its method of use.

In one aspect of the invention, an osteotomy guide is provided for indicating the femoral neck resection on a femur during hip surgery. The femur includes a shaft, a neck extending from the shaft, and a head arising from the neck at the proximal end of the femur. The femoral shaft extends along an anatomic axis from its proximal end to its distal end. A greater trochanter defines the superior-lateral aspect of the femur and the neck and greater trochanter define a trochanteric fossa between them. The osteotomy guide includes a first indexing feature alignable with a first anatomic landmark, a second indexing feature connected to the first indexing feature and alignable with a second anatomic landmark, an extension extending from the first indexing feature, and a resection guide connected to the extension and spaced from the first indexing feature for indicating the resection relative to the indexing features.

In another aspect of the invention, an osteotomy guide includes an elongated handle, an outrigger extending at an angle from the handle, a paddle mounted on the outrigger for indicating the resection level, and a probe extending beyond the paddle and being engageable with the trochanteric fossa.

In another aspect of the invention, a method for determining the resection level for the femoral neck includes providing an osteotomy guide having a first indexing feature alignable with a first anatomic landmark, a second indexing feature connected to the first indexing feature and alignable with a second anatomic landmark, an extension extending from the first indexing feature, and a resection guide connected to the extension and spaced from the first indexing feature for indicating a resection level relative to the indexing features; inserting the second indexing feature and resection guide into a surgical opening; engaging the second indexing feature with the trochanteric fossa; aligning the first indexing feature parallel to the anatomic axis of the femur outside of the surgical opening; and cutting the femoral neck at the resection level indicated by the resection guide.

BRIEF DESCRIPTION OF THE DRAWINGS

Various examples of the present invention will be discussed with reference to the appended drawings. These drawings depict only illustrative examples of the invention and are not to be considered limiting of its scope.

FIG. 5 is a sectional view of the osteotomy guide of FIG. 2 taken along line 5-5 of FIG. 4;

FIG. 6 is a sectional view like that of FIG. 5 showing a detail of the guide's function;

FIG. 7 is a sectional view of the osteotomy guide of FIG. 2 taken along line 7-7 of FIG. 4.

DESCRIPTION OF THE ILLUSTRATIVE EXAMPLES

Figures 1, 2:
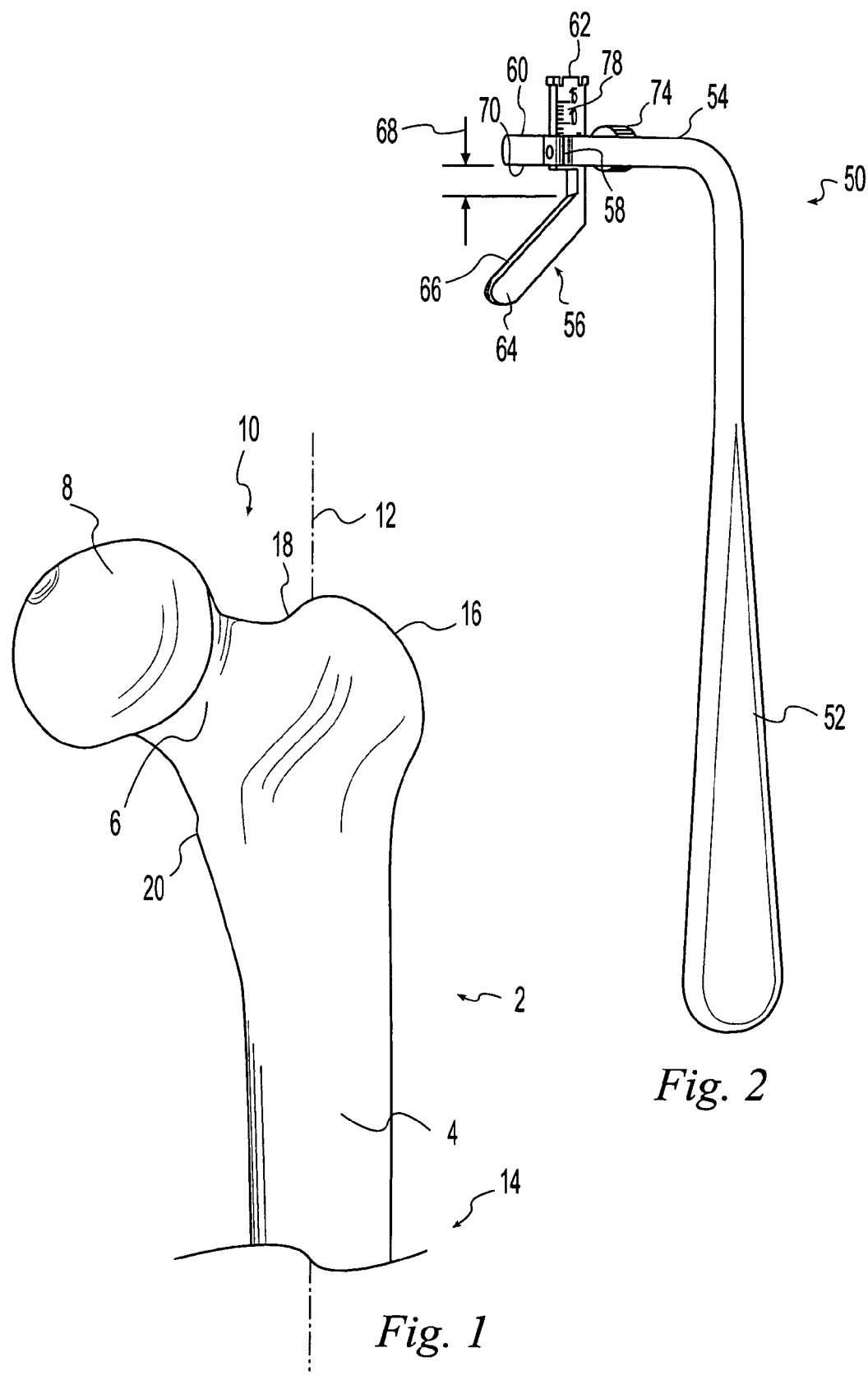
FIG. 1 is a perspective view of a femoral bone.
FIG. 2 is a perspective view of an exemplary osteotomy guide according to the present invention.
Figures 3, 4:
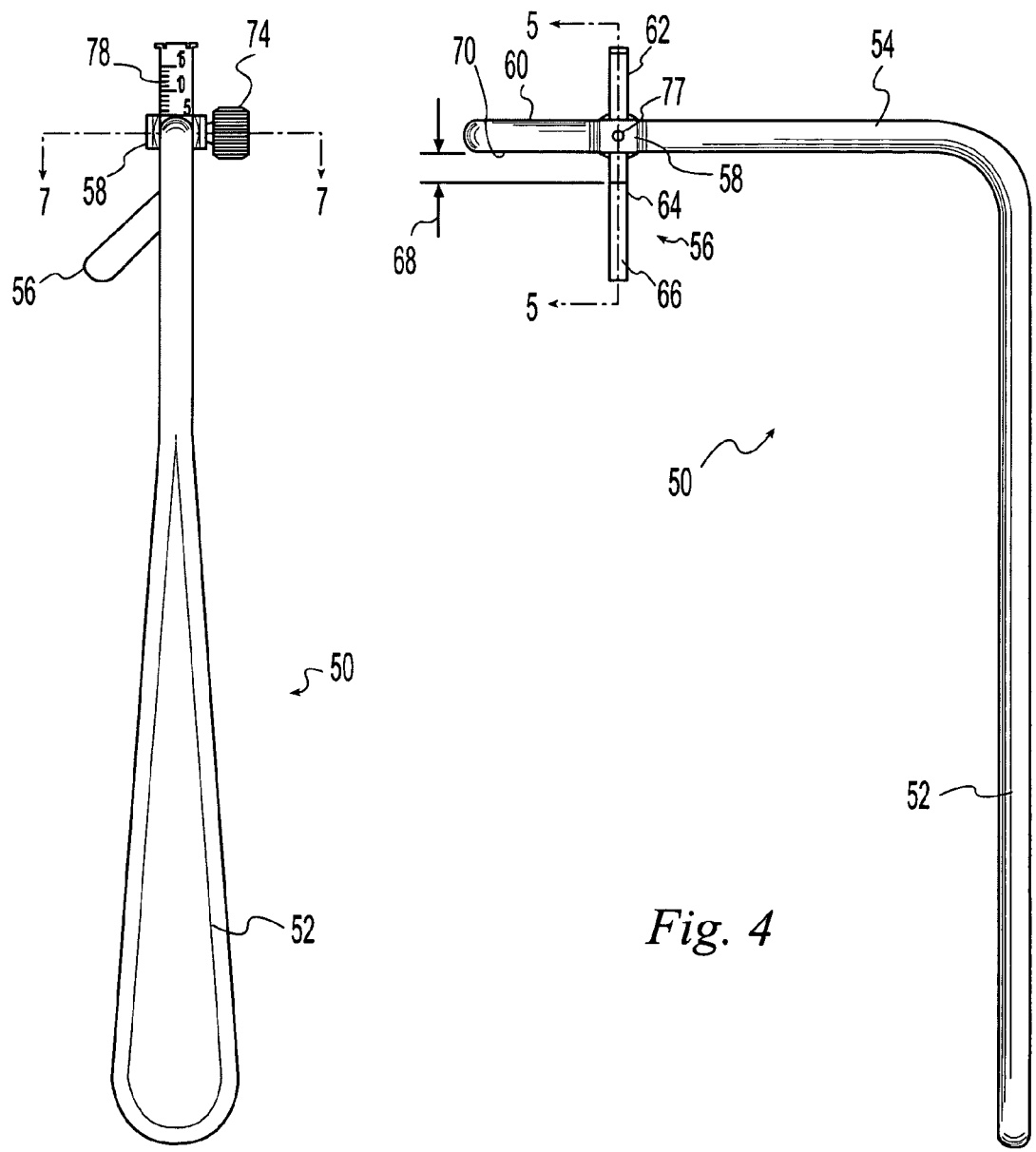
FIG. 3 is a front elevation view of the osteotomy guide of FIG. 2.
FIG. 4 is a side elevation view of the osteotomy guide of FIG. 2.

FIG. 1 depicts an anterior-medial view of a femur 2 having a shaft 4, a neck 6 extending from the shaft, and a head 8 arising from the neck 6 at the proximal end 10 of the femur. The femoral shaft 4 extends along an anatomic axis 12 from its proximal end 10 to its distal end 14. The anatomic axis 12 corresponds approximately to the centerline of the femoral shaft 4. The greater trochanter 16 forms a bulge, or hump, at the superior-lateral aspect of the femur 2. The neck 6 and greater trochanter 16 define a notch or trochanteric fossa 18 where they meet. The lesser trochanter 20 forms a bulge on the posterior-medial aspect of the femur 2 distal of the femoral neck 6. A portion of the lesser trochanter 20 is seen projecting from the posterior-medial aspect of the femur 2 in FIG. 1.

Embodiments of osteotomy guides according to the present invention include a first indexing feature alignable with a first anatomic landmark, a second indexing feature alignable with a second anatomic landmark, and a resection guide for indicating a desired femoral neck resection relative to one or both of the indexing features. The indexing features may be configured to reference any of a number of anatomic landmarks including the anatomic axis 12 of the femur, the greater trochanter 16, the lesser trochanter 20, the trochanteric fossa 18, the perimeter of the femoral head 8, the center of the femoral head 8, and/or other suitable anatomic landmark. The indexing features may be in the form of and/or include a rod, bar, plate, slot, index mark, surface, view hole, probe, light beam, and/or other suitable indexing feature for aligning with and/or engaging an anatomic landmark. For example, the first indexing feature may define an elongated handle alignable parallel with the anatomic axis of the femur and the second indexing feature may define a rod-like projection engageable with the trochanteric fossa. The present inventors prefer the trochanteric fossa as a landmark, especially during minimally invasive hip surgery, since it is more readily available during such procedures. The greater and lesser trochanters can be difficult to see and/or palpate in the narrow confines of a minimally invasive procedure prior to removal of the femoral head. Likewise, during a minimally invasive procedure, the femoral head preferably remains buried in the acetabular fossa until after the neck is divided.

The resection guide may be in the form of and/or include a rod, bar, plate, slot, index mark, surface, view hole, probe, light beam and/or other feature for indicating the resection relative to one or both of the indexing features. The resection guide may be mounted to and/or connected to one or both of the indexing features. Multiple osteotomy guides may be provided with different relationships between the resection guide and indexing features to accommodate different implant sizes and/or implanted positions. The resection guide may be mounted in a fixed position or it may be adjustably mounted on the osteotomy guide. For example, the resection guide may be mounted for selective movement between multiple positions relative to one or both of the indexing features. The resection guide may include markings to indicate the spacing of the resection guide from one or both of the indexing features in each of the multiple positions. The resection guide may be angled to correspond to an angular cut to be made on the neck. The resection guide may be rotatable between a position suitable for a left femur and a position suitable for a right femur. The osteotomy guide may include a retention mechanism to limit the travel of the resection guide and/or prevent the resection guide from being inadvertently removed from the osteotomy guide. The retention mechanism may permit selective disassembly of the resection guide from the osteotomy guide. The resection guide may include a staked assembly, ball detent, stop pin, screw, tab, and/or other suitable retention mechanism. For example, the retention mechanism may include flexible tabs to permit selective removal of the resection guide from the osteotomy guide.

The resection guide and/or second indexing feature may be mounted on, or formed adjacent to, the first indexing feature. Alternatively, the resection guide and/or second indexing feature may be mounted or formed on an outrigger that spaces the resection guide and/or second indexing feature from the first indexing feature such as to facilitate inserting the resection guide and/or second indexing feature into an incision.

The osteotomy guide may be made of metal, plastic, and/or other materials suitable for intraoperative contact with the surgical opening. For example, the osteotomy guide may be made of stainless steel.

In use, the surgeon may use preoperative templating to determine the desired femoral implant size, offset, head/neck length, and/or position. The surgeon may further make note of the relationship of the femoral neck resection relative to a suitable anatomic landmark. For example, the surgeon may note the distance from the trochanteric fossa down to the neck resection. The surgeon may then select an osteotomy guide according to the present invention that has the desired relationship between the indexing features and the resection guide. Alternatively, for an adjustable osteotomy guide, the surgeon may adjust the relationship between the indexing features and the resection guide to match the templated relationship. The indexing features are aligned with the anatomic landmarks. The surgeon then uses the resection guide to mark the femoral neck for a subsequent cut and/or uses the resection guide to directly guide the cut.

FIGS. 2-8 depict an exemplary osteotomy guide 50 according to the present invention. The exemplary osteotomy guide 50 is configured to index to the anatomic axis 12 and trochanteric fossa 18, however, the osteotomy guide 50 may be configured to index to other anatomic landmarks. Furthermore, while the exemplary osteotomy guide 50 is configured to facilitate minimally invasive surgery, it is also suitable for use in traditional open surgical approaches to the joint.

The osteotomy guide 50 includes a first indexing feature in the form of an elongated handle 52. An extension in the form of an outrigger 54 extends at an angle from the handle 52. While a variety of angles may be suitable, and the angle may vary to accommodate different landmarks, the exemplary outrigger 54 extends at a preferred angle of 90 degrees such that with the handle 52 positioned on the anterior side of the femur 2 and positioned parallel to the femoral anatomic axis 12, the outrigger 54 extends posteriorly toward the hip joint. A resection guide, in the form of a paddle 56, is mounted on the outrigger 54 for indicating the resection. Preferably the paddle 56 indicates both the resection level and the resection angle. The paddle is mounted for vertical translation within a hollow mounting 58 formed integrally with the outrigger 54. A second indexing feature in the form of a cylindrical probe 60 extends from the outrigger 54 and, in the exemplary embodiment, is integrally formed with the outrigger 54. The probe 60 extends straight from the outrigger 54 to engage the trochanteric fossa 18, however, it may also extend at an angle and it may define other shapes to accommodate different anatomic landmarks and/or surgical approaches.

The paddle 56 is partly "L"-shaped, being shaped like a hockey stick, with a first, vertical, leg 62 and a second, angled, leg 64. The first and second legs 62, 64 define an included angle. The second leg 64 includes a top surface defining a reference surface 66 for indicating the femoral resection level and angle. The included angle between the first and second legs 62, 64 is chosen to correspond to a desired resection angle to accommodate different implant designs and surgical techniques. For example, the angle may vary from 90 to 180 degrees to indicate resections from horizontal to vertical. More particularly, the angle may vary from 110 to 160 degrees to indicate the angled resections required by typical hip implants. The illustrative paddle 56 has an included angle of approximately 135 degrees. The reference surface 66 is spaced a known distance 68 from the bottom 70 of the probe 60. The first leg 62 slides within an opening 72 (FIG. 5) in the mounting 58. Preferably the first leg 62 and opening 72 have complimentary non-round cross sections so that the paddle 56 is constrained to vertical translation only without being permitted to rotate. In the exemplary embodiment, the first leg 62 and opening 72 have complimentary rectangular cross-sections (FIG. 7). A thumb screw 74 threads into a first hole 76 communicating with the opening 72 such that by tightening the thumb screw 74 against the first leg 62, the paddle is locked in a fixed position relative to the mounting 58 and consequently the probe 60. The mounting 58 includes a second hole 77, opposite the first hole 76, communicating with the opening 72 such that the thumb screw 74 may be alternatively positioned in the first 76 and second 77 holes to accommodate left and right handed users. The first leg 62 further includes a scale 78 that indicates the vertical spacing of the reference surface 66 relative to the bottom 70 of the probe 60. In the embodiment of FIGS. 2-8, the scale 78 indicates the spacing as measured along the centerline of the first leg 62 corresponding to the side 80 of a notch 82 (FIG. 5) formed in the first leg 62. The notch 82 defines an indention in the first leg 62 adjacent the intersection of the first and second legs 62, 64. The side 80 of the notch 82 defines a vertical wall that intersects the reference surface 66. The scale 78 indicates the vertical spacing from the bottom 70 of the probe 60 to this intersection.

The notch 82 further permits the paddle 56 to be reversed for use on left and right hip joints. Over most of its travel, the first leg 62 is constrained to translation only within the rectangular opening 72 (FIG. 5). However, by raising the paddle 56 until the notch 82 clears the top of the opening 72 (FIG. 6), the paddle 56 can be rotated and lowered to reengage the opening 72 180 degrees from its original position.

The paddle 56 is retained in the opening 72 by the thumb screw 74. However, by loosening the thumb screw 74, the paddle 56 may be removed by sliding it downwardly and out of the opening 72. The exemplary paddle 56 includes optional tabs 84 extending outwardly from the top of the first leg 62 to catch on the top of the mounting 58 adjacent the opening 72 and prevent the paddle 56 from inadvertently sliding out of the mounting 58. Notches 86 are formed inboard of the tabs 84 and extend from the top of the first leg 62 downwardly such that the tabs 84 are cantilevered and can be sprung inwardly. Thus, to remove the paddle 56 from the mounting 58, the tabs 84 are pressed inwardly until they clear the top of the mounting 58 and then the paddle 56 can be pulled downwardly from the mounting 58.

Figure 8:
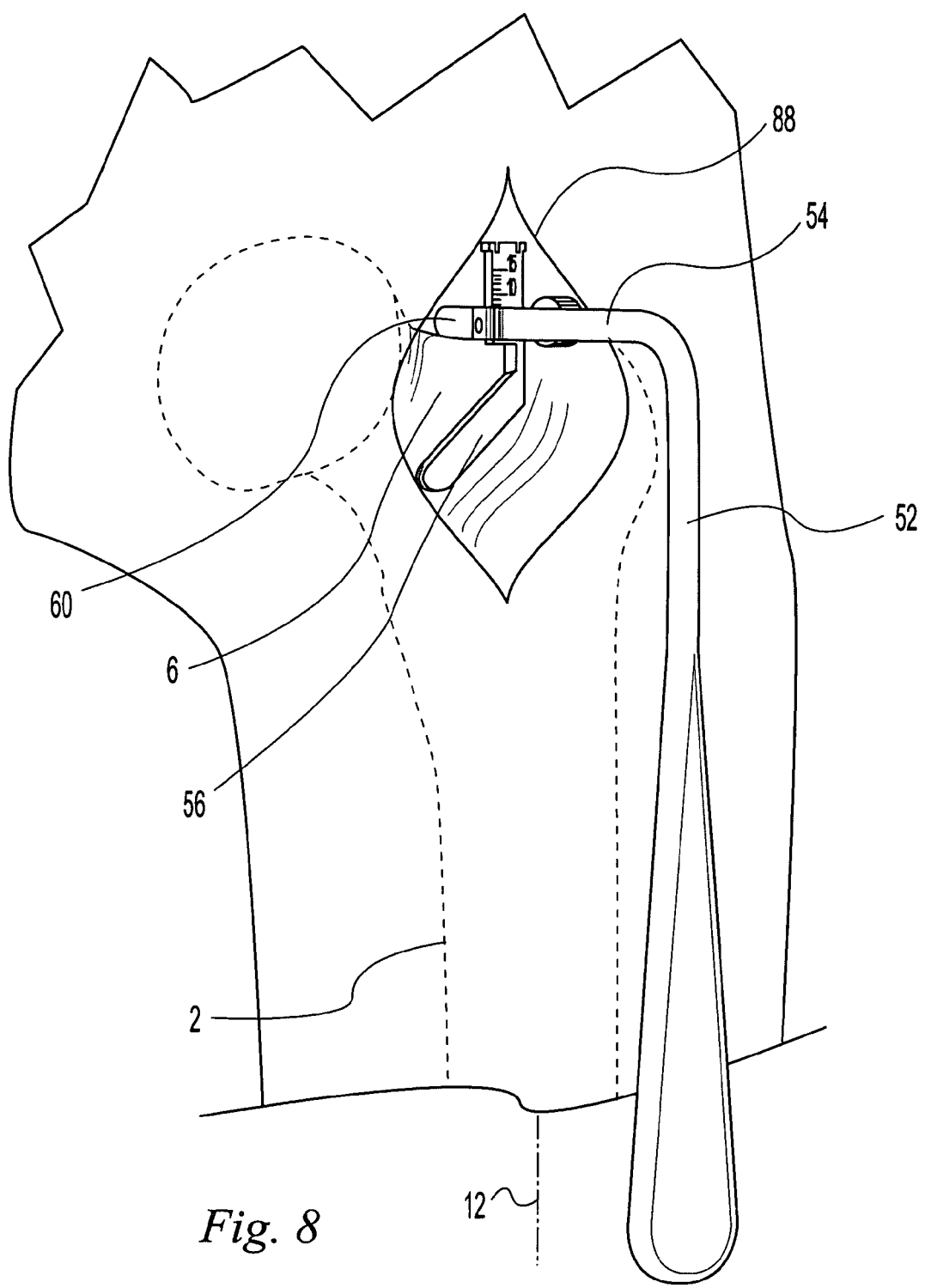
FIG. 8 is a perspective view showing the osteotomy guide of FIG. 1 engaged with the femoral bone of FIG. 1 in a minimally invasive surgical procedure.

In use, the surgeon uses preoperative templating to determine the desired femoral implant size, offset, head/neck length, and/or position. The surgeon notes the vertical distance from the trochanteric fossa down to the chosen femoral neck resection level. He then adjusts the paddle 56 within the mounting 58 so that the scale 78 indicates this distance. The probe 60 and paddle 56 are inserted into the surgical opening to position them adjacent the proximal femur 10. FIG. 8 depicts an anterior-lateral approach to the hip joint through a small incision 88 in a minimally invasive procedure. The probe 60 and paddle 56 are inserted into the incision 88. The narrow configuration of the probe 60 and paddle 56 facilitates positioning them adjacent to the proximal femur 10 in such procedures. Furthermore, the offset from the handle 52 to the probe 60 and paddle 56 provided by the narrow outrigger 54 extending posteriorly permits the handle 52 to remain outside of the surgical opening. Thus, there is no need to position all of the osteotomy guide adjacent the bone where it is difficult to access or to position all of the osteotomy guide outside of the surgical opening where it is far from the bone and thus difficult to accurately indicate the resection level. The bottom 70 of the probe 60 is engaged with the trochanteric fossa 18 and the handle 52 is aligned parallel with the anatomic axis 12 of the femur 2. The surgeon then uses the reference surface 66 of the paddle 56 to guide a saw blade, surgical pen, and/or other device to mark and/or cut the femoral neck 6.

Although examples of an osteotomy guide and its use have been described and illustrated in detail, it is to be understood that the same is intended by way of illustration and example only and is not to be taken by way of limitation. The invention has been illustrated in use to measure and mark the resection level of the femoral neck relative to the trochanteric fossa of the femur. However, the osteotomy guide may be configured to reference other landmarks of the hip joint. Accordingly, variations in and modifications to the navigated surgical sizing guide and its use will be apparent to those of ordinary skill in the art, and the following claims are intended to cover all such modifications and equivalents.

What is claimed is:

1. An osteotomy guide for indicating the femoral neck resection on a femur having a shaft, a neck extending from the shaft, and a head arising from the neck at the proximal end of the femur, the femoral shaft extending along an anatomic axis from its proximal end to its distal end, a greater trochanter defining the superior-lateral aspect of the femur, the neck and greater trochanter defining a trochanteric fossa between them, the osteotomy guide comprising:
   an elongated handle;
   an outrigger extending at an angle from the handle;
   a paddle mounted on the outrigger for indicating the resection level; and
   a probe extending beyond the paddle and being engageable with the trochanteric fossa, whereby, with the probe engaging the trochanteric fossa, the elongated handle extends along side the femoral shaft, wherein the paddle includes a first leg and a second leg, the first and second legs defining an angle, the second leg having a top surface defining a reference surface spaced a known distance from the probe, wherein the first leg slides within an opening in the outrigger, wherein the paddle includes a notch, the notch permitting the paddle to be rotated 180 degrees when the paddle is raised such that the notch clears the top of the opening, wherein the paddle further comprises tabs extending outwardly from the top of the first leg, the tabs engaging the outrigger adjacent the opening to prevent the paddle from sliding out of the opening, wherein the paddle further comprises notches formed inboard of the tabs and extending from the top of the first leg downwardly such that the tabs are cantilevered and can be sprung inwardly to allow the paddle to be removed from the opening.

2. The osteotomy guide of claim 1 wherein the outrigger extends at an angle of approximately 90 degrees such that with the handle positioned on the anterior side of the femur and positioned parallel to the femoral axis, the outrigger extends posteriorly toward the hip joint.

3. The osteotomy guide of claim 1 wherein the paddle is mounted to the osteotomy guide for vertical translation relative to the probe.

4. The osteotomy guide of claim 3 further comprising a locking mechanism for selectively preventing vertical translation of the paddle relative to the probe.

5. The osteotomy guide of claim 1 wherein the angle between the first and second legs is approximately 45 degrees.

6. The osteotomy guide of claim 1 wherein the first leg further includes a scale that indicates the vertical spacing of the reference surface relative to the probe.

7. The osteotomy guide of claim 1 wherein the first leg and the opening have complimentary non-round cross sections such that the paddle is constrained to vertical translation within the outrigger.

* * * * *

UNITED STATES PATENT AND TRADEMARK OFFICE
CERTIFICATE OF CORRECTION

PATENT NO.       : 7,582,091 B2                                   Page 1 of 1
APPLICATION NO.  : 11/230072
DATED            : September 1, 2009
INVENTOR(S)      : Duncan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 917 days.

Signed and Sealed this

Fourteenth Day of September, 2010

David J. Kappos
*Director of the United States Patent and Trademark Office*